United States Patent [19]

Goldman et al.

[11] 4,107,326

[45] Aug. 15, 1978

[54] NOVEL BENZYLIDENEAMINOGUANIDINES

[75] Inventors: Leon Goldman; Yang-i Lin, both of Nanuet; Joseph William Marsico, Jr., Pearl River, all of N.Y.

[73] Assignee: American Cyanamid Company, Stamford, Conn.

[21] Appl. No.: 794,600

[22] Filed: May 6, 1977

[51] Int. Cl.$^2$ ............... A61K 31/155; C07C 121/60; C07C 133/10
[52] U.S. Cl. ............... 424/304; 260/465 E; 260/501.14; 260/564 F; 424/316; 424/326
[58] Field of Search ........... 260/564 F, 465 E, 501.14; 424/326, 316, 304

[56] References Cited

U.S. PATENT DOCUMENTS

| | | | |
|---|---|---|---|
| 3,657,337 | 4/1972 | Houlihan et al. | 260/564 F |
| 3,658,993 | 4/1972 | Kodama et al. | 424/326 |
| 3,769,432 | 10/1973 | Tomcufcik | 424/326 |
| 3,975,533 | 8/1976 | Kodama | 424/326 |

FOREIGN PATENT DOCUMENTS 1,048,812   11/1966   United Kingdom ............ 260/564 F

*Primary Examiner*—Gerald A. Schwartz
*Attorney, Agent, or Firm*—Edward A. Conroy, Jr.

[57] ABSTRACT

This disclosure describes novel substituted benzylideneaminoguanidines useful as anti-hypertensive agents and as diuretics.

20 Claims, No Drawings

NOVEL BENZYLIDENEAMINOGUANIDINES

BRIEF SUMMARY OF THE INVENTION

This invention relates to new organic compounds and, more particularly, is concerned with novel substituted benzylideneaminoguanidines which may be represented by the following structural formula:

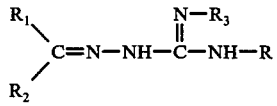

wherein $R_1$ is 2,6-dichlorophenyl, 2,4-dichlorophenyl, 2,6-dimethylphenyl, 3,4-dimethylphenyl, 3-cyanophenyl, 3,4,5-trimethoxyphenyl or 2,4,6-triethoxyphenyl; $R_2$ is hydrogen or methyl; $R_3$ is hydrogen, methyl, ethyl, benzyl or dimethylaminomethylene; and R is a moiety of the formulae:

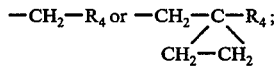

wherein $R_4$ is phenyl, p-fluorophenyl, p-chlorophenyl, 2,6-difluorophenyl or m-trifluoromethylphenyl. The invention also includes novel compositions of matter containing the abovedefined compounds useful as hypotensive agents and/or as diuretics and the method of meliorating hypertension and/or enhancing the excretion of sodium ions in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, N,N-di-methyl formamide, acetone, chloroform, ethyl acetate, and the like. They are appreciably soluble in non-polar organic solvents such as toluene, carbon tetrachloride, and the like but are relatively insoluable in water. The organic bases of this invention form non-toxic acid-addition salts with variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention wherein $R_3$ is hydrogen, methyl, ethyl or benzyl may exist in other tautomeric forms as follows:

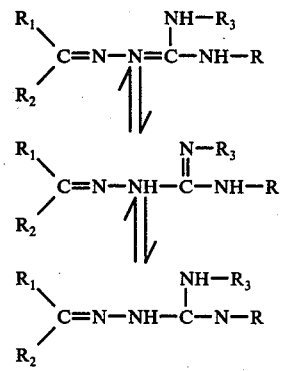

In addition, when $R_3$ is dimethylaminomethylene then the novel compounds exist in the following tautomeric forms:

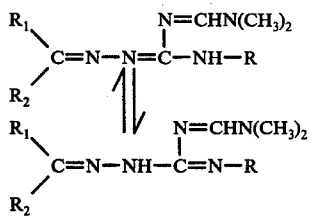

For purposes of this invention, all such tautomeric forms are equivalent.

The novel compounds of the present invention are physiologically active and therefore useful in the pharmaceutical field. In particular, the compounds of this invention are useful because they possess not only long lasting hypotensive activity but also diuretic and natriuretic properties. They differ from most of the known effective diuretic agents, however, in that the compounds of this invention greatly enhance the exretion of sodium ions with only a slight increase in excretion of potassium ions. The potassium loss, which is caused by known diuretics, often results in a severe muscular weakness. Since the compounds of this invention are essentially free of this potassium depletion effect, they have this decided advantage as diuretics. As diuretic agents, they can be used for the treatment of edema, hypertension and other diseases known to be responsive to this therapy.

The novel compounds of the present invention were shown to possess oral activity in vivo as hypotensive agents and as diuretics (producing significant water diuresis and $Na^+$ loss but with sparing of $K^+$) as determined in the following procedure. One to three adult spontaneously hypertensive rats are dosed by gavage with a test compound at a dose of 100 mg./kg. of body weight and loaded with 0.9% NaCl at 25 ml./kg. of body weight at zero hour. The 0–5 hour urine is collected and $Na^+$, $K^+$ and $Cl^-$ concentrations analyzed. A second identical dose of test compound is given without NaCl loading at 24 hours. The mean arterial blood pressure is measured directly by femoral artery puncture at 28 hours. The results with representative compounds of the present invention are given in Table I below wherein the reduction in mean arterial blood pressure is represented as:

$4+ = 100-110$ mm.
$3+ = 111-120$ mm.
$2+ = 121-130$ mm.

1+ = 131-135 mm.
as contrasted to a control value of 165 mm. The sodium, potassium, and chloride levels are given in terms of milliequivalents (meq.) per 5 hours with a normal sodium control being 0.60 milliequivalents per 5 hours.

stomach and permits the inner component to pass intact into the duodenum or to be delayed in release. A variety of materials can be used for such enteric layers or coatings, such materials including a number of polymeric acids or mixtures of polymeric acids with such materials

TABLE I

| Compound | Reduction in mean arterial blood pressure | Diuretic Results | | | |
|---|---|---|---|---|---|
| | | Urine Vol. ml./5 Hrs. | Total meq./5 hours | | |
| | | | Na$^+$ | K$^+$ | Cl$^-$ |
| 1-Benzyl-3-(2,6-dichlorobenzylideneamino)-guanidine | 4+ | 14.0 | 1.34 | 0.53 | 1.48 |
| 1-Benzyl-3-(2,6-dichlorobenzylideneamino)-guanidine hemisuccinate | 2+ | 4.4 | 0.46 | 0.63 | 0.56 |
| 1-Benzyl-3-(2,6-dichlorobenzylideneamino)-guanidine diacetate | 4+ | 17.0 | 1.70 | 0.95 | 1.87 |
| 1-(2,6-Dichlorobenzylideneamino)-3-(p-fluorobenzyl)guanidine hydroiodide | 2+ | 11.4 | 1.09 | 0.55 | 1.28 |
| -Benzyl-3-[(3,4-dimethylbenzylidene)-amino]guanidine hydroiodide | 1+ 1.7 | 0.10 | 0.24 | 0.27 | |
| 1-Benzyl-(3-m-cyanobenzylideneamino)-guanidine | 2+ | 7.4 | 0.64 | 0.45 | 0.55 |
| 1,2-Dibenzyl-3-(2,6-dichlorobenzylidene-amino)guanidine hydrochloride | 2+ | 5.0 | 0.13 | 0.35 | 0.42 |
| 1-Benzyl-3-(2,6-dichlorobenzylideneamino)-2-methylguanidine | 4+ | 18.3 | 1.50 | 0.60 | 1.66 |
| 1-(2,6-Dichlorobenzylideneamino)-3-[m-(trifluoromethyl)benzylidene]guanidine hydrochloride | 1+ | 4.0 | 0.04 | 0.04 | 0.30 |
| 1-Benzyl-2-(2,6-dichlorobenzylideneamino)-3-(dimethylaminomethylene)guanidine hemi-fumarate | 2+ | 5.5 | 0.37 | 0.40 | 0.58 |
| 1-Benzyl-3-(2,4-dichlorobenzylideneamino)-guanidine | 2+ | 10.2 | 0.93 | 0.39 | 0.83 |
| 1-Benzyl-3-[(3,4,5-trimethoxy-α-methyl-benzylidine)amino]guanidine | 3+ | 1.0 | 0.08 | 0.16 | 0.08 |
| 1-Benzyl-3-(2,4,6-triethoxybenzylidene-amino)guanidine | 3+ | 2.5 | 0.18 | 0.37 | 0.16 |
| 1-{[1-(p-Chlorophenyl)cyclopropyl]methyl}-3-(2,6-dichlorobenzylideneamino)guanidine | 4+ | 18.0 | 1.60 | 0.56 | 1.69 |
| 1-(2,6-Dichlorobenzylideneamino)-3-(1-phenylcyclopropylmethyl)guanidine | 2+ | 13.0 | 0.95 | 0.35 | 1.05 |
| 1-Benzyl-3-(2,6-dimethylbenzylideneamino)-guanidine | 3+ | 11.5 | 0.99 | 0.58 | 1.22 |
| 1-(2,6-Dichlorobenzylideneamino)-3-(2,6-difluorobenzyl)guanidine | 1+ | 12.0 | 0.91 | 0.51 | 1.18 |
| 1-Benzyl-3-(2,6-dichlorobenzylideneamino)-2-ethylguanidine | 2+ | 12.6 | 0.98 | 0.60 | 1.16 |

The novel compounds of the present invention have thus been shown to be valuable hypotensive and diuretic agents of low toxicity when administered orally. The amount of a single dose or of a daily dose to be given will vary but should be such as to give a proportionate dosage of from about 5 mg. to about 100 mg. per day for a subject of about 70 kg. body weight. The dosage regimen may be adjusted to provide the optimum therapeutic response, for example, doses of 1.0–25 mg. may be administered on a 4 times a day regimen or the dose may be proportionately increased as indicated by the exigencies of the therapeutic situation.

The novel compounds of the present invention may be administered as active components of compositions for administration in unit dosage form as tablets, pills, capsules, powders, granules, oral solutions or suspensions and the like. For preparing solid compositions such as tablets, the principal active ingredient is mixed with conventional tableting ingredients such as core starch, lactose, sucrose, sorbiitol, talc, stearic acid, magnesium stearate, dicalcium phosphate, gums, and functionally similar materials as pharmaceutical diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The liquid forms in which the novel compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention. Examples of suitable oral unit dosage forms in accord with this invention are tablets, capsules, pills, powders, packets, granules, wafers, caches, teaspoonfuls, dropperfuls, ampules, vials, segregated multiples of any of the foregoing and other forms as herein described.

The novel compounds of the present invention (except where R₃ is dimethylaminomethylene) may be readily prepared in accordance with the following reaction scheme:

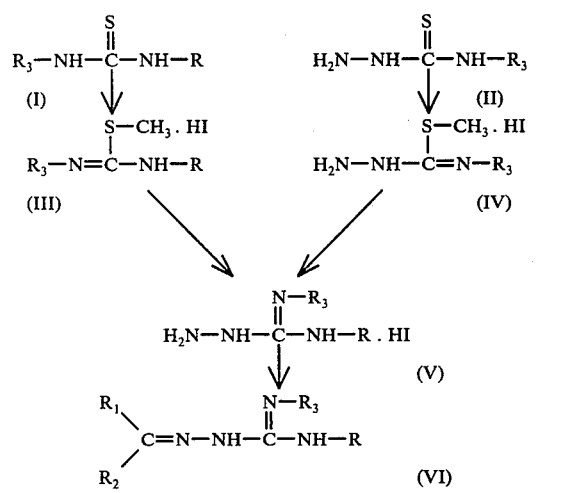

wherein $R_1$, $R_2$, and R are as hereinabove defined and $R_3$ is hydrogen, methyl, ethyl or benzyl. In accordance with the above reaction scheme, a 1,3-disubstituted-thiourea (I) or a 4-substituted-3-thiosemicarbazide (II) is treated with methyl iodide in ethanol as solvent at the reflux temperature for 12-24 hours to provide the corresponding 1,3-disubstituted-2-methylthiopseudourea hydroiodide (III) or methyl N-substituted-thiocarbazimidate hydroiodide (IV). Treatment of the 1,3-disubstituted-2-methylthiopseudourea hydroiodide (III) with hydrazine hydrate in ethanol as solvent at the reflux temperature for 4-8 hours provides the 1-amino-2,3-disubstituted-guanidine hydroiodide (V). Treatment of the methyl N-substituted-thiocarbazimidate hydroiodide (IV) with an amine of the formula: R-NH₂ in water as the solvent at steam bath temperature for a few hours also provides the 1-amino-2,3-disubstituted-guanidine hydroiodide (V). The 1-amino-2,3-disubstituted-guanidine hydroiodide (V) is neutralized with aqueous caustic and the liberated free base is extracted with an immiscible solvent and the extract is concentrated under reduced pressure. The residue is treated with a carbonyl compound of the formula: R₁-CO-R₂ in ethanol as solvent at the reflux temperature for 12-24 hours to provide the 1,2-disubstituted-3-benzylideneaminoguanidine (VI).

Those compounds of the present invention wherein R₃ is dimethylaminomethylene may be readily prepared by treating a compound of formula (VI) wherein R₃ is hydrogen with an excess of N,N-dimethylformamide dimethylacetal at 80°-120° C. for 2-6 hours. Some of the novel compounds of the present invention may also be prepared in accordance with the following reaction scheme:

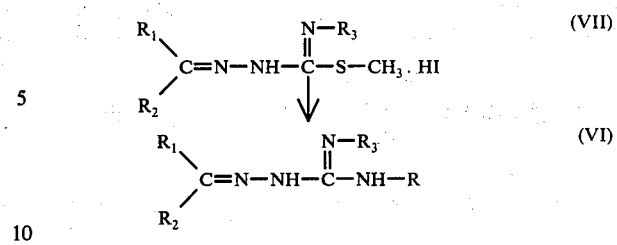

wherein $R_1$, $R_2$, and R are as hereinabove defined and $R_3$ is hydrogen, methyl, ethyl or benzyl. In accordance with the above reaction scheme, a methyl 3-(benzylidene)thiocarbazimidate hydroiodide (VII) [prepared as described in U.S. Pat. No. 3,657,337] is treated with an amine of the formula: R-NH₂ in ethanol as solvent at the reflux temperature for 4-8 hours to provide the 1,2-disubstituted-3-benzylideneaminoguanidine (VI).

A preferred embodiment of the present invention may be represented by the following general formula:

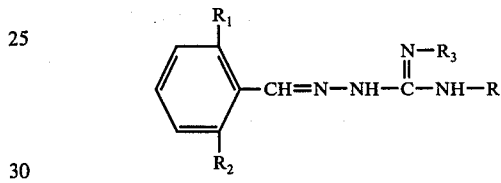

wherein $R_1$ and $R_2$ are the same and are chloro or methyl; $R_3$ is hydrogen, methyl, ethyl or benzyl; and R is a moiety of the formulae:

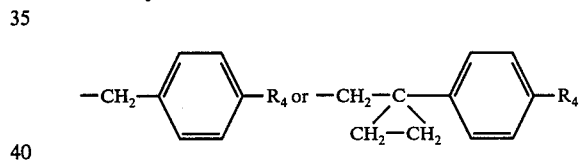

wherein $R_4$ is hydrogen, fluoro or chloro.

The invention will be described in greater detail in conjunction with the following specific examples.

EXAMPLE 1

1-Benzyl-3-(2,6-dichlorobenzylideneamino)guanidine

A solution of 93.6 g of methyl 3-(2,6-dichlorobenzylidene)thiocarbazimidate hydroiodide (U.S. Pat. No. 3,657,337) and 51.2 of benzylamine in 400 ml. of absolute ethanol is heated at reflux for 6 hours and then diluted while hot with 400 ml. of water, causing the separation of an oil. On standing, the oil crystallizes and the nearly colorless crystals are recovered by filtration. Recrystallization from aqueous ethanol gives the desired product as pale yellow crystals, m.p. 134°-137° C.

EXAMPLE 2

1-Benzyl-3-(2,6-dichlorobenzylideneamino)guanidine

A solution of 11.7 g. of methyl 3-(2,6-dichlorobenzylidene)thiocarbazimidate hydroiodide (U.S. Pat. No. 3,657,337) and 3.37 g. of benzylamine in 25 ml. of ethanol is heated at reflux for 18 hours and then evaporated to dryness under reduced pressure. The residue is partitioned between 80 ml. of diethyl ether and 100 ml. of water and the aqueous extract is made alkaline with ammonia. A pale yellow solid is recovered by filtration and recrystallized from aqueous ethanol, giving the desired product as colorless crystals, m.p. 133°-135° C.

EXAMPLE 3

1-Benzyl-3-(2,6-dichlorobenzylideneamino)guanidine diacetate

A mixture of 25.0 g. of 1-benzyl-3-(2,6-dichlorobenzylideneamino)guanidine and 15 ml. of glacial acetic acid in 100 ml. of absolute ethanol is heated briefly to solution and then diluted with 800 ml. of a 1:1 mixture of diethyl ether-petroleum ether (b.p. 35°-60° C.). On standing, crystallization occurs. The desired product is recovered by filtration as colorless crystals, m.p. 114°-119° C.

EXAMPLE 4

1-Benzyl-3-(2,6-dichlorobenzylideneamino)guanidine hydrochloride

To a solution of 2.00 g. of 1-benzyl-3-(2,6-dichlorobenzylideneamino)guanidine in 40 ml. of absolute ethanol is added 20 ml. of 3.75 N hydrogen chloride in isopropyl alcohol. The mixture is evaporated under reduced pressure, giving the desired product as a colorless solid, m.p. 58°-68° C.

EXAMPLE 5

1-Benzyl-3-(2,6-dichlorobenzylideneamino)guanidine hemisuccinate

A solution of 2.00 g. of 1-benzyl-3-(2,6-dichlorobenzylideneamino)guanidine and 0.370 g. of succinic acid in 50 ml. of methanol is evaporated under reduced pressure, giving the desired product as a light yellow solid, m.p. 70°-80° c.

EXAMPLE 6

1-Benzyl-2-(2,6-dichlorobenzylideneamino)-3-(dimethylaminomethylene)guanidine hemifumarate A solution of 2.00 g. of 1-benzyl-3-(2,6-dichlorobenzylideneamino)guanidine in 25 ml. of N,N-dimethylformamide dimethylacetal is heated at 100° C. for 3.5 hours and then evaporated under reduced pressure to a yellow gum. A mixture of this gum and 0.360 g. of fumaric acid in 10 ml. of absolute ethanol is heated on a steam bath and crystallization occurs. Cooling and filtration produce crystals which are recrystallized from absolute ethanol, giving the desired product as pale yellow crystals, sinters sharply at 132°-135° C., m.p. 153°-158° C. (dec.).

EXAMPLE 7

Methyl N-methylthiocarbazimidate hydroiodide

A stirred solution of 25.0 g. of 4-methyl-3-thiosemicarbazide and 35.5 g. of methyl iodide in 200 ml. of ethanol is heated under reflux for 18 hours. The reaction mixture is cooled, filtered and the filter cake is washed with diethyl ether and n-hexane, giving cream colored crystals. Recrystallization from ethanol, gives the desired product as cream colored crystals, m.p. 161°-165° C.

EXAMPLE 8

1-Amino-2-benzyl-3-methylguanidine hydroiodide

A solution of 36.0 g. of methyl N-methylthiocarbazimidate hydroiodide and 16.1 g. of benzylamine in 100 ml. of water is heated on a steam bath for one hour and then allowed to stand at room temperature overnight. The reaction mixture is concentrated under reduced pressure. The residue is dissolved in ethanol, treated with activated charcoal and filtered. The filtrate is concentrated to a small volume under reduced pressure and the residual solution is diluted with diethyl ether. The resultant crystals are recovered by filtration and recrystallized from a mixture of ethanol and diethyl ether, giving the desired product as pale pink crystals, m.p. 118°-119° C.

EXAMPLE 9

1-Benzyl-3-(2,6-dichlorobenzylideneamino)-2-methylguanidine

A mixture of 10.0 g. of 1-amino-2-benzyl-3-methylguanidine hydroiodide and 1:1 methylene chloride-hexane is shaken with excess 5N NaOH. The organic layer is passed through hydrous sodium magnesium silicate and concentrated under reduced pressure. The residue is dissolved in 100 ml. of ethanol, 5.73 g. of 2,6-dichlorobenzaldehyde is added and the resultant solution is heated under reflux for 18 hours. Water is added to the hot solution until turbid. The cooled mixture is filtered, giving cream colored crystals. Recrystallization from aqueous ethanol gives the desired product as nearly colorless crystals, m.p. 84°-86° C.

EXAMPLE 10

Methyl N-ethylthiocarbazimidate hydroiodide

A stirred solution of 97.0 g. of 4-ethyl-3-thiosemicarbazide and 127.8 g. of ethyl iodide in 500 ml. of ethanol is heated under reflux for 18 hours. The reaction mixture is concentrated under reduced pressure, diluted with n-hexane and filtered, giving the desired product as a nearly colorless solid, m.p. 73°-74° C.

EXAMPLE 11

1-Amino-2-benzyl-3-ethylguanidine hydroiodide

A solution of 25.0 g. of methyl N-ethylthiocarbazimidate hydroiodide and 10.2 g. of benzylamine in 150 ml. of water is heated on a steam bath for one hour and then evaporated under reduced pressure. The residue is dissolved in ethanol, treated with activated charcoal, filtered and evaporated under reduced pressure. The residue is dissolved in methylene chloride and the solution is passed through hydrous sodium magnesium silicate and concentrated under reduced pressure, giving the desired product as a residual red oil.

EXAMPLE 12

1-Benzyl-3-(2,6-dichlorobenzylideneamino)-2-ethylguanidine

A 10.0 g. portion of 1-amino-2-benzyl-3-ethylguanidine hydroiodide in a mixture of 100 ml. each of diethyl ether, n-hexane and methylene chloride is shaken with 10 ml. of 5N NaOH. A 5.46 g. portion of 2,6-dichlorobenzaldehyde is added and the mixture is shaken and then allowed to stand at room temperature overnight. The organic layer is washed with saturated aqueous sodium chloride, passed through hydrous sodium magnesium silicate and concentrated under reduced pressure. The residue is crystallized from diethyl ether-hexane to give the desired product as a bright yellow solid, m.p. 101°-103° C.

EXAMPLE 13

1,3-Dibenzyl-2-methylthiopseudourea hydroiodide

A solution of 25.6 g. of 1,3-dibenzylthiourea and 10 ml. of methyl iodide in 500 ml. of absolute ethanol is heated at reflux for 16 hours to give a solution of the desired product.

EXAMPLE 14

1-Amino-2,3-dibenzylguanidine hydroiodide

A solution of 6 ml. of hydrazine hydrate and the solution of 1,3-dibenzyl-2-methylthiopseudourea hydroiodide from Example 13 in 500 ml. of absolute ethanol is heated at reflux for 4 hours and then evaporated to dryness under reduced pressure. The residual solid is crystallized from isopropyl alcohol twice giving the desired product as colorless crystals, m.p. 135°–137° C.

EXAMPLE 15

1,2-Dibenzyl-3-(2,6-dichlorobenzylideneamino)guanidine hydrochloride

A solution of 3.50 g. of 2,6-dichlorobenzaldehyde and 7.64 g. of 1-amino-2,3-dibenzylguanidine hydroiodide in 250 ml. of absolute ethanol and 10 ml. of glacial acetic acid is heated at reflux for 8 hours. The solvent is removed under reduced pressure and the residual yellow oil is dissolved in 150 ml. of absolute ethanol. The solution is made basic with concentrated $NH_4OH$ and filtered, giving 7.0 g. of 1,2-dibenzyl-3-(2,6-dichlorobenzylideneamino)guanidine as colorless crystals, m.p. 148°–150° C.

An ethanol solution of the above compound is treated with hydrogen chloride, causing separation of an oil. On standing, the oil crystallizes and is filtered, giving colorless crystals which are recrystallized from aqueous ethanol, giving the desired product as colorless crystals, m.p. 178°–180° C.

EXAMPLE 16

1-(2,6-Dichlorobenzylideneamino)-3-(1-phenylcyclopropylmethyl)guanidine

A solution of 7.80 g. of methyl 3-(2,6-dichlorobenzylidene)thiocarbazimidate hydroiodide and 4.37 of 1-phenylcyclopropanemethylamine in 100 ml. of n-butanol and 25 ml. of water is heated at reflux for 24 hours. The solution is cooled, diluted with water to a final volume of 2 liters and is allowed to stand. Filtration gives a tan solid which is dissolved in ethyl acetate and purified by silica gel column chromatography. Crystallization of the product from diethyl ether gives the desired final product as colorless crystals, m.p. 136.5°–138.5° C.

EXAMPLE 17

1-{[1-(p-Chlorophenyl)cyclopropyl]methyl}-3-(2,6-dichlorobenzylideneamino)guanidine A solution of 7.80 g. of methyl 3-(2,6-dichlorobenzylidene)thiocarbazimidate hydroiodide and 4.37 g. of 1-(p-chlorophenyl)cyclopropanemethylamine in 100 ml. of n-butanol and 25 ml. of water is heated at reflux for 24 hours. The solution is cooled, diluted with water to a final volume of 2 liters and allowed to stand. Filtration gives a tan solid which is dissolved in ethyl acetate and purified by silica gel column chromatography. Crystallization of the product from diethyl ether gives the desired final product as colorless crystals, m.p. 126°–128° C.

EXAMPLE 18

1-(2,6-Dichlorobenzylideneamino)-3-(p-fluorobenzyl)-guanidine hydroiodide

A solution of 5.85 g. of methyl 3-(2,6-dichlorobenzylidene)thiocarbazimidate hydroiodide (U.S. Pat. No. 3,657,337) and 3.75 g. of p-fluorobenzylamine in 25 ml. of absolute ethanol is heated under reflux for 24 hours and then evaporated under reduced pressure, giving a mixture of gum and crystals. This mixture is dissolved in 50 ml. of absolute ethanol and diluted with 175 ml. of diethyl ether. The colorless plates which form are removed by filtration and discarded. The filtrate is diluted with petroleum ether (b.p. 30°–60° C), causing colorless needles to separate. These needles are removed by filtration and recrystallized from a mixture of ethanol-diethyl ether-petroleum ether (b.p. 30°–60° C), giving the desired product as colorless crystals, m.p. 162.5°–164° C.

EXAMPLE 19

2,6-Difluorobenzylamine hydrochloride

A mixture of 5.00 g. of 2,6-difluorobenzonitrile and 1.0 g. of 50% water-wet 5% palladium on carbon catalyst in 100 ml. of concentrated HCl and 100 ml. of absolute ethanol is shaken at room temperature under 20 lbs. pressure of hydrogen for 48 hours. The mixture is filtered and the filtrate is diluted with 500 ml. of diethyl ether and allowed to stand. Filtration gives the desired product as colorless crystals, m.p. 197°–200° C.

EXAMPLE 20

1-(2,6-Dichlorobenzylideneamino)-3-(2,6-difluorobenzyl)guanidine

A solution of 7.80 g. of methyl 3-(2,6-dichlorobenzylidene)thiocarbazimidate hydroiodide (U.S. Pat. No. 3,657,337) and 2.86 g. of 2,6-difluorobenzylamine (prepared from 2,6-difluorobenzylamine hydrochloride) in 100 ml. of n-butanol and 20 ml. of water is heated at reflux for 66 hours. The solvent is removed under reduced pressure and the residual yellow oil is dissolved in aqueous ethanol and made basic with 10N NaOH. The resultant mixture is extracted with chloroform and the chloroform extract is evaporated under reduced pressure to give a yellow gum. This gum in ethyl acetate is purified by silica gel column chromatography, giving a colorless solid. This solid is recrystallized from aqueous ethanol, giving the desired product as colorless crystals, m.p. 168.5°–169.5° C.

EXAMPLE 21

1-(2,6-Dichlorobenzylideneamino)-3-[m-(trifluoromethyl)-benzylidene]guanidine hydrochloride A solution of 4.88 g. of methyl 3-(2,6-dichlorobenzylidene)thiocarbazimidate hydroiodide (U.S. Pat. No. 3,657,337) and 4.37 g. of m-(trifluoromethyl)benzylamine [F. N. Freidfelder and Y. H. Ng, J. Pharm. Sci., 54, 1204 (1965)] in 270 ml. of absolute ethanol is heated at reflux for 18 hours. The solution is cooled, made basic with 2N NaOH and the solvent is removed under reduced pressure. The yellow residue is triturated with dichloromethane and the triturate is evaporated under reduced pressure to give a yellow oil. A diethyl ether solution of this oil is treated with ethanolic hydrogen chloride. Filtration gives colorless crystals which are recrystallized from ethanol-diethyl ether, giving the desired product as colorless crystals, m.p. 165°–167° C.

EXAMPLE 22

1-Benzyl-3-(2,4-dichlorobenzylideneamino)guanidine

A 10.0 g. portion of 1-amino-3-benzylguanidine hydroiodide in a mixture of 100 ml. each of diethyl ether, hexane and methylene chloride is shaken with 10 ml. of 5N NaOH. A 5.98 g. portion of 2,4-dichlorobenzaldehyde is added and and the mixture is shaken for 15 minutes. The organic layer is washed with saturated aqueous sodium chloride, passed through hydrous sodium magnesium silicate and concentrated to dryness under reduced pressure. The residue is crystallized from methylene chloride-hexane, giving the desired product as cream colored crystals, m.p. 139°–141° C.

EXAMPLE 23

1-Benzyl-3-(2,6-dimethylbenzylideneamino)guanidine

A solution of 1.34 g. of 2,6-dimethylbenzaldehyde [G. Lock and K. Schmidt, J. Prakt. Chem., 140, 229 (1934)] and 2.92 g. of 1-amino-3-benzylguanidine hydroiodide in 25 ml. of absolute ethanol is heated at reflux for 18 hours. The solution is evaporated under reduced pressure to give a syrup which is made alkaline with aqueous NaOH. The mixture is extracted with chloroform. The chloroform extract is evaporated under reduced pressure to give a yellow syrup. Trituration of this syrup with diethyl ether and n-hexane, followed by filtration, gives the desired product as light pink crystals, m.p. 125°–126° C.

EXAMPLE 24

1-Benzyl-3-[(3,4-dimethylbenzylidene)amino]guanidine hydroiodide

A mixture of 2.68 g. of 3,4-dimethylbenzaldehyde and 5.84 g. of 1-amino-3-benzylguanidine hydroiodide [W. J. Finnegan, R. A. Henry and E. Lieber, J. Org. Chem., 18, 779 (1953)] in 30 ml. of 66% aqueous ethanol is heated under reflux for 3 hours and then allowed to cool and crystallize. Filtration gives nearly colorless crystals which are recrystallized from aqueous ethanol, giving the desired product as cream-colored crystals, m.p. 183°–185° C.

EXAMPLE 25

1-Benzyl-3-(m-cyanobenzylideneamino)quanidine

A mixture of 2.62 g. of m-cyanobenzaldehyde and 5.84 g. of 1-amino-3-benzylguanidine hydroiodide [W. J. Finnegan, R. A. Henry and E. Lieber, J. Org. Chem., 18, 779 (1953)] in 30 ml. of 66% aqueous ethanol is heated under reflux for 7.5 hours and then allowed to cool and crystallize. Filtration gives light tan crystals which are dissolved by heating in 100 ml. of absolute ethanol. The hot solution is treated with 5.00 ml. of 10N NaOH and diluted with 100 ml. of water. Chilling and filtration give pale yellow crystals which are recrystallized from 150 ml. of 50% aqueous ethanol, giving the desired product as pale yellow crystals, m.p. 155.5°–157.5° C.

EXAMPLE 26

1-Benzyl-3-[(3,4,5-trimethoxy-α-methylbenzylidene)amino]-guanidine

Excess 5N NaOH is added to 10.0 g. of 1-amino-3-benzylguanidine hydroiodide. The resultant free base is extracted into methylene chloride. The organic layer is passed through hydrous sodium magnesium silicate and concentrated under reduced pressure. To this is added 50 ml. of ethanol and 4.1 g. of 3,4,5-trimethoxyacetophenone and the solution is heated under reflux for 18 hours. Water is added to the hot solution until turbid. Cooling and filtration give crystals which are recrystallized from aqueous ethanol, giving the desired product as nearly colorless crystals, m.p. 107°–109° C.

EXAMPLE 27

1-Benzyl-3-(2,4,6-triethoxybenzylideneamino)guanidine

A mixture of 10.0 g. of 1-amino-3-benzylguanidine hydroiodide and 100 ml. each of diethyl ether, n-hexane and methylene chloride is shaken with 10 ml. of 5N NaOH. To this is added 8.15 g. of 2,4,6-triethoxybenzaldehyde and the mixture is shaken for 15 minutes. The organic layer is washed with saturated aqueous sodium chloride, passed through hydrous sodium magnesium silicate and concentrated to dryness under reduced pressure. The residue is crystallized from aqueous ethanol, giving the desired product as nearly colorless crystals, m.p. 140°–141° C.

EXAMPLE 28

| | Preparation of 50 mg. Tablets | |
|---|---|---|
| Per Tablet | Tablets | Per 10,000 |
| 0.050 gm. | 1-(p-fluorobenzyl)-3-(2,4-dichlorobenzylideneamino)-2-ethylguanidine | .500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1-(p-fluorobenzyl)-3-(2,4-dichlorobenzylideneamino)-2-ethylguanidine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 29

| Preparation of Oral Suspension | |
|---|---|
| Ingredient | Amount |
| 1-{[1-(p-fluorophenyl)cyclopropyl]-methyl}-3-(2,6-dimethylbenzylideneamino)-2-methylguanidine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |

| Preparation of Oral Suspension | |
|---|---|
| Ingredient | Amount |
| Distilled water qs to | 100 ml. |

The sorbitol solution is added to 40 ml. of distilled water and the 1-{[1-(p-fluorophenyl)cycloproply]methyl}-3-(2,6-dimethylbenzylideneamino)-2-methylguanidine is suspended therein. The saccharin, sodium benzoate, flavor and dye are added and dissolved. The volume is adjusted to 100 ml. with distilled water. Each ml. of syrup contains 5 mg. of 1-{[1-(p-fluorophenyl)cyclopropyl]methyl}-3-(2,6-dimethylbenzylideneamino)-2-methylguanidine.

We claim:

1. A compound selected from the group consisting of those of the formula:

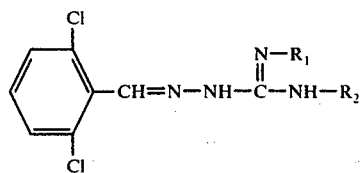

wherein $R_1$ is hydrogen, methyl, ethyl or benzyl and $R_2$ is a moiety of the formulae:

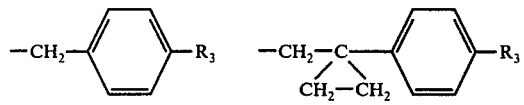

wherein $R_3$ is hydrogen, fluoro or chloro; the tautomers thereof and the pharmacologically acceptable acid-addition salts thereof.

2. The compound according to claim 1 wherein $R_1$ is hydrogen and $R_2$ is benzyl.

3. The compound according to claim 1 wherein $R_1$ is methyl and $R_2$ is benzyl.

4. The compound according to claim 1 wherein $R_1$ is ethyl and $R_2$ is benzyl.

5. The compound according to claim 1 wherein $R_1$ is benzyl and $R_2$ is benzyl.

6. The compound according to claim 1 wherein $R_1$ is hydrogen and $R_2$ is 1-phenylcyclopropylmethyl.

7. The compound according to claim 1 wherein $R_1$ is hydrogen and $R_2$ is 1-(p-chlorophenyl)cyclopropylmethyl.

8. The compound according to claim 1 wherein $R_1$ is hydrogen and $R_2$ is p-fluorobenzyl.

9. A compound selected from the group consisting of 1-(m-trifluoromethylbenzyl)-2-ethyl-3-[(2,4-dichloro-α-methylbenzylidene)amino]guanidine, the tautomers thereof and the pharmacologically acceptable acid-addition salts thereof.

10. A compound selected from the group consisting of 1-(p-fluorobenzyl)-2-dimethylaminomethylene-3-(3-cyanobenzylideneamino)guanidine, the tautomers thereof and the pharmacologically acceptable acid-addition salts thereof.

11. A compound selected from the group consisting of 1-(2,6-difluorobenzyl)-2-methyl-3-[(3,4,5-trimethoxy-α-methylbenzylidene)amino]guanidine, the tautomers thereof and the pharmacologically acceptable acid-addition salts thereof.

12. A compound selected from the group consisting of 1-(m-trifluoromethylbenzyl)-3-(2,4,6-triethoxybenzylideneamino)guanidine, the tautomers thereof and the pharmacologically acceptable acid-addition salts thereof.

13. A compound selected from the group consisting of 1-[1-(p-fluorophenyl)cyclopropylmethyl]-2-methyl-3-[(2,4-dichloro-α-methylbenzylidene)amino]guanidine, the tautomers thereof and the pharmacologically acceptable acid-addition salts thereof.

14. A compound selected from the group consisting of 1-benzyl-3-(2,4-dichlorobenzylideneamino)guanidine, the tautomers thereof and the pharmacologically acceptable acid-addition salts thereof.

15. A compound selected from the group consisting of 1-benzyl-3-(m-cyanobenzylideneamino)guanidine, the tautomers thereof and the pharmacologically acceptable acid-addition salts thereof.

16. A compound selected from the group consisting of 1-benzyl-3-[(3,4,5-trimethoxy-α-methylbenzylidene)amino]guanidine, the tautomers thereof and the pharmacologically acceptable acid-addition salts thereof.

17. A compound selected from the group consisting of 1-benzyl-3-(2,4,6-triethoxybenzylideneamino)guanidine, the tautomers thereof and the pharmacologically acceptable acid-addition salts thereof.

18. The method of lowering elevated blood pressure in a mammal which comprises administering orally to said mammal an effective amount of a compound selected from the group consisting of those of the formula:

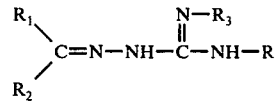

wherein $R_1$ is selected from the group consisting of 2,6-dichlorophenyl, 2,4-dichlorophenyl, 2,6-dimethylphenyl, 3,4-dimethylphenyl, 3-cyanophenyl, 3,4,5-trimethoxyphenyl and 2,4,6-triethoxyphenyl; $R_2$ is hydrogen or methyl; $R_3$ is selected from the group consisting of hydrogen, methyl, ethyl, benzyl and dimethylaminomethylene; and R is a moiety of the formulae:

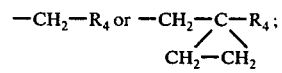

wherein $R_4$ is selected from the group consisting of phenyl, p-fluorophenyl, p-chlorophenyl, 2,6-difluorophenyl and m-trifluoromethylphenyl; the tautomers thereof and the pharmacologically acceptable acid-addition salts thereof.

19. The method of enhancing the excretion of sodium ions in a mammal which comprises administering orally to said mammal an effective amount of a compound selected from the group consisting of those of the formula:

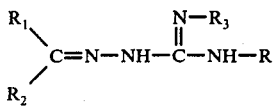

wherein $R_1$ is selected from the group consisting of 2,6-dichlorophenyl, 2,4-dichlorophenyl, 2,6-dimethylphenyl, 3,4-dimethylphenyl, 3-cyanophenyl, 3,4,5-trimethoxyphenyl and 2,4,6-triethoxyphenyl; $R_2$ is hydrogen or methyl; $R_3$ is selected from the group consisting of hydrogen, methyl, ethyl, benzyl and dimethylaminomethylene; and R is a moiety of the formulae:

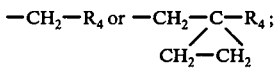

wherein $R_4$ is selected from the group consisting of phenyl, p-fluorophenyl, p-chlorophenyl, 2,6-difluorophenyl and m-trifluoromethylphenyl; the tautomers thereof and the pharmacologically acceptable acid-addition salts thereof.

20. A therapeutic composition in oral dosage unit form useful for lowering elevated blood pressure and/or enhancing the excretion of sodium ions in mammals comprising from about 5 mg. to about 100 mg. per daily dosage unit, in association with a pharmaceutical carrier, of a compound selected from the group consisting of those of the formula:

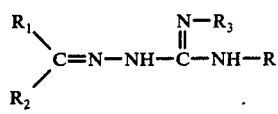

wherein $R_1$ is selected from the group consisting of 2,6-dichlorophenyl, 2,4-dichlorophenyl, 2,6-dimethylphenyl, 3,4-dimethylphenyl, 3-cyanophenyl, 3,4,5-trimethoxyphenyl and 2,4,6-triethoxyphenyl; $R_2$ is hydrogen or methyl; $R_3$ is selected from the group consisting of hydrogen, methyl, ethyl, benzyl and dimethylaminomethylene; and R is a moiety of the formulae:

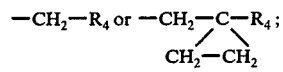

wherein $R_4$ is selected from the group consisting of phenyl, p-fluorophenyl, p-chlorophenyl, 2,6-difluorophenyl and m-trifluoromethylphenyl; the tautomers thereof and the pharmacologically acceptable acid-addition salts thereof.

* * * * *